US010513673B2

(12) United States Patent
Lang et al.

(10) Patent No.: US 10,513,673 B2
(45) Date of Patent: *Dec. 24, 2019

(54) CHLORINE BLEACHING AFTER PERACID TREATMENT

(71) Applicant: Ecolab USA Inc., Saint Paul, MN (US)

(72) Inventors: Jason Lang, Saint Paul, MN (US); Benjamin Crew, Saint Paul, MN (US); Jonathan P. Fast, Saint Paul, MN (US); Angela Becker, Saint Paul, MN (US); Steven Lundberg, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/015,391

(22) Filed: Jun. 22, 2018

(65) Prior Publication Data
US 2018/0371375 A1 Dec. 27, 2018

Related U.S. Application Data

(60) Provisional application No. 62/523,474, filed on Jun. 22, 2017.

(51) Int. Cl.
*C11D 3/00* (2006.01)
*C11D 3/39* (2006.01)
(Continued)

(52) U.S. Cl.
CPC ............ *C11D 3/3945* (2013.01); *A61L 2/186* (2013.01); *C11D 3/3942* (2013.01);
(Continued)

(58) Field of Classification Search
CPC ......... D06F 37/00; D06F 35/00; C11D 3/945; C11D 3/044; C11D 7/06; C11D 11/0017; C11D 3/48; C11D 3/395; A61L 2/186
See application file for complete search history.

(56) References Cited

U.S. PATENT DOCUMENTS 6,262,013 B1   7/2001  Smith et al.
7,682,403 B2 *  3/2010  Gohl .................. C11D 3/39
                                              8/111
(Continued)

FOREIGN PATENT DOCUMENTS

EP    1302108 A2   2/2002
WO    9103590 A1   3/1991
(Continued)

OTHER PUBLICATIONS

Ecolab USA Inc., PCT/US2018/038963 filed Jun. 22, 2018, "Notification of Transmittal of the International Search Report and the Written Opinion of the International Searching Authority, or the Declaration", 15 pages, dated Sep. 25, 2018.

*Primary Examiner* — Eisa B Elhilo
(74) *Attorney, Agent, or Firm* — McKee, Voorhees, Sease, PLC

(57) ABSTRACT

A method for enhancing bleaching efficacy for treatment of articles, including for example laundry is disclosed. Methods for antimicrobial disinfecting and/or sanitizing and bleaching laundry and other articles is provided by washing the articles with a peroxyformic acid composition at a first pH for effective antimicrobial efficacy, thereafter applying an alkaline source to increase the pH for addition of a bleaching component. The methods can be provided as part of a laundry operation and can be utilized in industrial and commercial applications.

18 Claims, 4 Drawing Sheets

(51) Int. Cl.
  *A61L 2/18* (2006.01)
  *C11D 11/00* (2006.01)
  *C11D 3/395* (2006.01)

(52) U.S. Cl.
  CPC ........ *C11D 3/3953* (2013.01); *C11D 11/0017* (2013.01); *A61L 2202/26* (2013.01)

(56) References Cited

U.S. PATENT DOCUMENTS

| | | |
|---|---|---|
| 9,228,158 B2 | 1/2016 | Tinker et al. |
| 2005/0153859 A1* | 7/2005 | Gohl ................ C11D 3/39 510/302 |
| 2013/0047345 A1* | 2/2013 | Fast ................ C11D 3/39 8/137 |
| 2014/0047647 A1 | 2/2014 | Berman et al. |

FOREIGN PATENT DOCUMENTS

| | | |
|---|---|---|
| WO | 2014031478 A1 | 2/2014 |
| WO | 2016100694 A1 | 6/2016 |

* cited by examiner

CHLORINE BLEACHING AFTER PERACID TREATMENT

CROSS-REFERENCE TO RELATED APPLICATIONS

This application claims priority to provisional application U.S. Ser. No. 62/523,474 filed Jun. 22, 2017, which is incorporated herein by reference in its entirety.

FIELD OF THE INVENTION

Methods for enhancing bleaching efficacy following use of a peroxyformic acid composition for antimicrobial efficacy, i.e. sanitizing or disinfecting of articles, namely laundry, are provided. In particular, laundry can be treated by washing the laundry with a peroxyformic acid composition at a first pH for effective antimicrobial efficacy, thereafter applying a bleaching component without negatively interfering with the bleaching component due to the beneficial composition of the peroxyformic acid composition, and lastly draining the remaining components of the peroxyformic acid composition, and the bleaching agent from the laundry. Beneficially, this method for antimicrobial efficacy and bleaching laundry can be provided as part of a laundry operation and can be utilized in industrial and commercial applications. Still further beneficially, this method for antimicrobial efficacy and bleaching laundry can be utilized as a part of a laundry application that provides disinfection against various difficult to treat organisms and at various temperatures, including low temperatures. In particular, performic acid (PFA) has an advantageous formulation over other oxygen bleaches, peracetic acid (PAA), hydrogen peroxide and/or other peroxycarboxylic acid formulations when bleaching with sodium hypochlorite or other species that would react with hydrogen peroxide.

BACKGROUND OF THE INVENTION

In industrial and commercial laundry facilities, textile materials such as sheets, towels, wipes, garments, table cloths, etc. are often laundered at elevated temperatures and at alkaline pH. Alkalinity can be provided through a single alkaline detergent, or alternatively alkalinity can be provided from one product, while the other detergent components, including surfactants, chelants, water conditioners and/or other detergent materials are provided in a second product. In other markets, textile materials are often laundered with neutral detergents with a separate alkaline product combined in a wash. Detergents can be combined in a laundry application with various additional components such as bleaches, brightening agents, anti-redeposition agents, etc. that are used to enhance the appearance of the resulting textile materials. Various additional components may optionally be dosed separately from the alkaline detergent, and will either be mixed together in the laundry wash bath or in a separate laundry bath liquor. For example, in some laundry applications there are discrete dosing and rinsing steps where there is a rinse between a detergent and bleach step. In other laundry applications, such as a tunnel washer, various addition steps employing mixing of the components. In each of these applications at the end of the cycle, the textile materials that have been treated with an alkaline detergent are typically treated with a commercial or industrial sour composition that contains acid components for neutralizing alkaline residues on the fabric to enhance skin compatibility.

In a conventional, industrial laundry washing facility, textile materials can be subjected to several treatment steps in an industrial sized laundry washing machine to provide antimicrobial efficacy. Exemplary treatment steps include a presoak step, a wash step that often occurs at a pH of about 11 to 12, a rinse step and/or multiple rinse steps for the removal of soil containing wash liquor which incrementally lower the pH, and a sour step that brings the final pH to about 5 to 7, and an extract step that often involves spinning the textiles and/or pressing the textiles in a tunnel application to remove water. An antimicrobial composition can be applied concurrently with the detergent, such as an all-in-one product for powders and solids or concurrent dosing of distinct products, immediately following the detergent step, following a rinse and drain, and/or during the sour step where it is afforded a minimum contact time in the absence of other cleaning chemicals. Laundry applications can vary between concurrent dosing of detergent and other cleaning chemicals.

There remains a need to improve the industrial laundry washing techniques and provide a reduction in processing time, cost of materials, materials consumption, energy costs, and water consumption. Accordingly, it is an objective of the methods to improve on one or more of these aspects of laundry washing techniques.

An object of the methods to enhance bleaching efficacy for laundry and other applications employing an antimicrobial step before a bleaching step.

A further object of the methods is to provide a low oxygen bleaching system for the sanitizing or antimicrobial disinfecting methods of use. The low oxygen peroxyformic acid compositions are suitable for use with chlorine bleach. An object of the methods is to enable bleaching efficacy of a chlorine bleach in combination with the peroxyformic acid composition for bleaching of laundry articles. In the presence of the peroxyformic acid composition the chlorine bleach is allowed to provide bleaching efficacy, as opposed to the interference with bleaching efficacy that customarily takes place with oxygen-containing (or greater oxygen-containing) antimicrobials. Low hydrogen peroxide containing peroxyformic acid compositions are beneficially provided in the bleaching of laundry methods to avoid such interaction with chlorine as is customary with peroxycarboxylic acids, such as peroxyacetic acid formulations. In still further benefits and aspects of the methods, peroxyformic acid compositions, regardless of the hydrogen peroxide content, provide benefits when combined with chlorine in comparison to other peroxycarboxylic acids (e.g. peroxyacetic acid) due to the improved efficacy enabling lower dosing of the peroxyformic acid composition as well as rapid degradation of the peroxyformic acid composition.

Other objects, advantages and features of the methods will become apparent from the following specification taken in conjunction with the accompanying drawings.

BRIEF SUMMARY OF THE INVENTION

An advantage of the methods of antimicrobial efficacy, i.e. sanitizing and/or disinfecting, and bleaching laundry with the combination of steps of treating laundry including a first peroxyformic acid treatment followed by a pH adjustment to increase pH before a bleaching step, is that the peroxyformic acid does not negatively interact with chlorine bleaching components. The methods provide an upfront disinfection of the laundry in a wash program before pH adjustment to provide a chlorine bleach or other bleaching component and provide good bleaching efficacy. A method for treating laundry is provided according to the methods. More particularly, a method for antimicrobial efficacy and bleaching laundry is provided.

A laundry antimicrobial, sanitizing and/or disinfecting and bleaching process is provided where the peroxyformic acid composition is dosed first, followed by a bleaching step. In some aspects, the peroxyformic acid composition is provided with separate products containing surfactants, builders and other low-alkaline detergent compositions. This differs from conventional usage by placing the sanitizing or antimicrobial step prior to the bleaching and employing a lower concentration of the peroxycarboxylic acid to achieve the antimicrobial step, providing various benefits afforded by the use of the peroxyformic acid: 1) chlorine bleaching component can be used following the antimicrobial peroxycarboxylic acid without negative interaction with the hydrogen peroxide in the antimicrobial agent; 2) peroxyformic acid compositions require lower actives in comparison to other peroxycarboxylic acid compositions, such as C2 peracetic acid and other medium to long chain fatty acid antimicrobial composition, and degrade in the wash application more rapidly; and 3) peroxyformic acid compositions are suitable for providing low temperature disinfection and antimicrobial efficacy.

In an embodiment, a method of antimicrobial sanitizing and/or disinfecting and bleaching laundry comprises: (a) washing the laundry with a peroxyformic acid composition at a pH range from about 4 to about 7 in a laundry washing machine for effective antimicrobial efficacy on the laundry; thereafter (b) adding an alkalinity source to the washing machine to increase the pH range to at least about 7 in the laundry washing machine; thereafter (c) applying a chlorine bleach component in the laundry washing machine; and (d) draining the peroxyformic acid composition and the chlorine bleach component from the laundry. In further aspects, the peroxyformic acid composition is applied to the laundry in the laundry washing machine at a pH from about 5 to about 7, or from about 6 to about 7, or about 7, for about 3 to about 15 minutes, or for about 5 to about 10 minutes. In a further aspect, the peroxyformic acid composition is provided to the laundry washing machine at an actives level from about 5 ppm to about 100 ppm, or preferably from about 5 ppm to about 20 ppm. In an aspect, the alkalinity source increases the pH range to at least above 10, from about 10 to about 11, or at least about 11. In a further aspect, the chlorine bleach component is applied to the laundry in the laundry washing machine for about 3 to about 15 minutes, or for about 5 to about 10 minutes. In a further aspect, the laundry is rinsed with water in the laundry washing machine for at least about 1 minute, or from about 1 minute to about 6 minutes. Beneficially, the methods of antimicrobial sanitizing and/or disinfecting and bleaching laundry disinfects the laundry and removes bacteria, viruses or other contaminants from the laundry. The method can beneficially provide effective low temperature antimicrobial and bleaching efficacy, including wherein the temperature of the washing machine is less than about 120° F.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
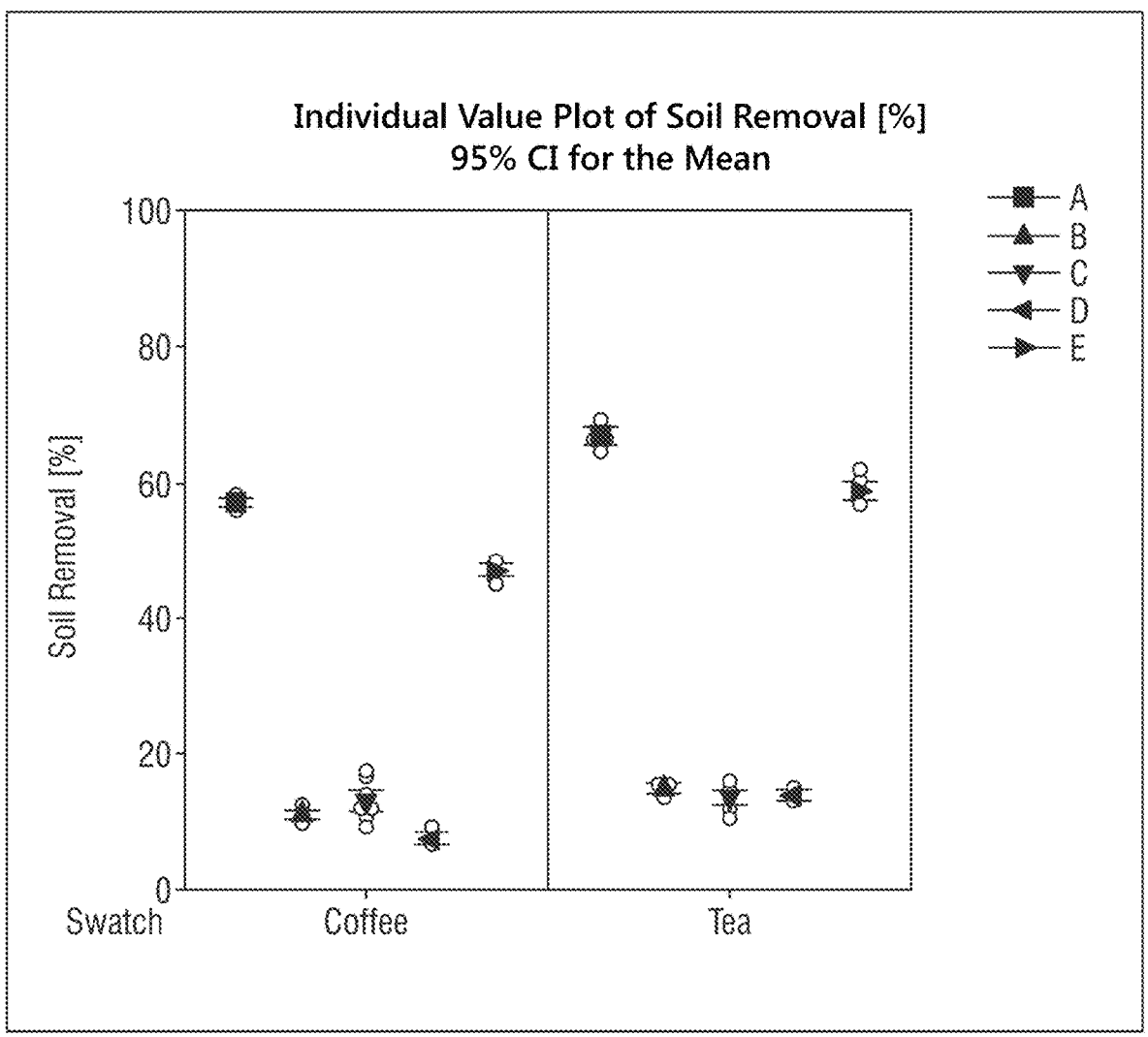
FIG. 1 shows a plot of soil removal efficacy evaluated according to embodiments of the methods.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

Embodiments of the methods provide significant benefits over use of conventional peroxyacetic acid (PAA) for the disinfection of textiles. Importantly, as disclosed herein, peroxyformic acid (PFA) can be used at much lower concentrations and temperatures when compared to PAA. This allows upfront disinfection in a wash program with a PFA formula and then adjustment of the pH and add a chlorine bleach component to bleach the textile and still achieve bleaching efficacy. However, if one were to disinfect upfront in a wash program with a PAA formula and then adjust pH and add chlorine bleach to bleach the textile, the large amount of peroxide that is a part of the PAA formula will react with the sodium hypochlorite (or chlorine bleaching component). The reaction of hydrogen peroxide and sodium hypochlorite will prevent the sodium hypochlorite from being able to bleach the textile, requiring a significant increase in the amount of the sodium hypochlorite (or bleaching component) to be used for adequate bleaching.

The embodiments of this invention are not limited to particular methods of incorporating a bleaching step in an antimicrobial laundering application, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

An "antiredeposition agent" refers to a compound that helps keep soil suspended in water instead of redepositing onto the object being cleaned. Antiredeposition agents are useful in the present methods to assist in reducing redepositing of the removed soil onto the surface being cleaned.

As used herein, the term "cleaning" refers to a method used to facilitate or aid in soil removal, bleaching, microbial population reduction, rinsing, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2).

The terms "include" and "including" when used in reference to a list of materials refer to but are not limited to the materials so listed. The term "laundry" refers to items or articles that are cleaned and/or reduction of microbial population in a laundry washing machine. In general, laundry refers to any item or article made from or including textile materials, woven fabrics, non-woven fabrics, and knitted fabrics. The textile materials can include natural or synthetic fibers such as silk fibers, linen fibers, cotton fibers, polyester fibers, polyamide fibers such as nylon, acrylic fibers, acetate fibers, and blends thereof including cotton and polyester blends. The fibers can be treated or untreated. Exemplary treated fibers include those treated for flame retardancy. It should be understood that the term "linen" is often used to describe certain types of laundry items including bed sheets, pillow cases, towels, table linen, table cloth, bar mops and uniforms. It should be understood that the term "linen" is often used to describe certain types of laundry items including bed sheets, pillow cases, towels, table linen, table cloth, bar mops and uniforms.

As used herein, the term "peracid" may also be referred to as a "peroxycarboxylic acid", "percarboxylic acid" or "peroxyacid." Sulfoperoxycarboxylic acids, sulfonated peracids and sulfonated peroxycarboxylic acids are also included within the term "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Patent Publication Nos. 2010/0021557, 2010/0048730 and 2012/0052134 which are incorporated herein by reference in their entireties. A peracid refers to an acid having the hydrogen of the hydroxyl group in carboxylic acid replaced by a hydroxy group. Oxidizing peracids may also be referred to herein as peroxycarboxylic acids.

As used herein, the term "polymer" generally includes, but is not limited to, homopolymers, copolymers, such as for example, block, graft, random and alternating copolymers, terpolymers, and higher "x" mers, further including their derivatives, combinations, and blends thereof. Furthermore, unless otherwise specifically limited, the term "polymer" shall include all possible isomeric configurations of the molecule, including, but are not limited to isotactic, syndiotactic and random symmetries, and combinations thereof. Furthermore, unless otherwise specifically limited, the term "polymer" shall include all possible geometrical configurations of the molecule.

The term "soft surface" refers to a resilient cleanable substrate, for example materials made from woven, nonwoven or knit textiles, leather, rubber or flexible plastics including fabrics (for example surgical garments, draperies, bed linens, bandages, etc.), carpet, transportation vehicle seating and interior components and the like. As referred to herein laundry and linens are included in soft surfaces.

As used herein, the term "soil" refers to polar or non-polar organic or inorganic substances including, but not limited to carbohydrates, proteins, fats, oils and the like. These substances may be present in their organic state or complexed to a metal to form an inorganic complex.

As used herein, the term "stain" refers to a polar or non-polar substance which may or may not contain particulate matter such as metal oxides, metal hydroxides, metal oxide-hydroxides, clays, sand, dust, natural matter, carbon black, graphite and the like As used in this disclosure, the term "sporicide" refers to a physical or chemical agent or process having the ability to cause greater than a 90% reduction (1-log order reduction) in the population of spores of *Bacillus cereus* or *Bacillus subtilis* within a defined time frame and temperature set by the relevant regulatory authority. In certain embodiments, the sporicidal compositions of the invention provide greater than a 99% reduction (2-log order reduction), greater than a 99.99% reduction (4-log order reduction), or greater than a 99.999% reduction (5-log order reduction) in such population.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. The efficacy according to the methods is effective against a broad range of bacteria, including gram positive and gram negative. Exemplary bacteria include for example, *Escherichia* spp., *Staphylococcus* spp., *Klebsiella* spp., *Enterococcus* spp., *Acinetobacter* spp., *Pseudomonas* spp., *Streptococcus* spp., including for example *Escherichia Coli, Staphylococcus*

*aureus*, methicillin-resistant *Staphylococcus aureus* (MRSA), *Staphylococcus epidermidis, Klebsielle Pneumonia* including *Carbapenem Resistant Klebsielle Pneumonia, Enterococcus faecalis, Enterococcus hirae, Acinetobacter baumannii, Pseudomonas aeruginosa, Streptococcus pyogenes, Mycobacterium terrae,* and *Mycobacterium avium*. In addition to bacteria it is understood that viruses, fungi, Mycobacteria, yeast and spores can also be treated by the methods disclosed herein.

As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "threshold agent" refers to a compound that inhibits crystallization of water hardness ions from solution, but that need not form a specific complex with the water hardness ion. Threshold agents include but are not limited to a polyacrylate, a polymethacrylate, an olefin/maleic copolymer, and the like.

The term "water soluble" refers to a compound that can be dissolved in water at a concentration of more than 1 wt. %. The terms "sparingly soluble" or "sparingly water soluble" refer to a compound that can be dissolved in water only to a concentration of 0.1 to 1.0 wt. %. The term "water insoluble" refers to a compound that can be dissolved in water only to a concentration of less than 0.1 wt. %.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods, systems, and compositions of the present invention may comprise, consist essentially of, or consist of the components and ingredients of the present invention as well as other ingredients described herein. As used herein, "consisting essentially of" means that the methods, systems, and compositions may include additional steps, components or ingredients, but only if the additional steps, components or ingredients do not materially alter the basic and novel characteristics of the claimed methods, systems, and compositions.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

Methods of Antimicrobial Treatment (Sanitizing and/or Disinfecting) and Bleaching Laundry Washing Machines A method for treating laundry is provided. A laundry washing machine is provided for use in the methods. The laundry washing machine includes a drum having an interior for holding laundry, a motor constructed and arranged for rotating the drum, a water inlet for introducing water into the drum interior, a chemical inlet for introducing chemicals into the drum interior, a drain for allowing fluid to drain from the drum interior, and a processing unit constructed for operating the laundry washing machine. The processing unit can be constructed to provide a washing cycle for washing laundry, an antimicrobial, sanitizing and/or disinfecting and bleaching cycle (which may be before or after the washing cycle), and a detergent use solution cycle for removing soil from the laundry. Beneficially, the use of the antimicrobial peroxyformic acid composition does not negatively interfere with the bleaching efficacy of the chlorine bleach.

The method for treating laundry can be provided in a commercial and/or industrial laundry washing facility and can be provided in a residential and/or home laundry washing machine that is programmable. Exemplary commercial and/or industrial laundry washing facilities include those cleaning textiles for the rental, health care, and hospitality industries. In addition, the method for treating laundry can occur as part of an operation that includes additional steps, such as, washing, rinsing, finishing, and extracting. In addition, it should be understood that the step of treating laundry can include, as part of the step, additional activities such as, for example, washing and finishing.

Many commercial and industrial laundry washing machines are capable of handling the methods for treating laundry. Many commercial and industrial laundry washing machines are computer programmable, and computer programs can be provided to operate the machines. In addition, it is expected that machines can be made available to treat laundry according to the methods, and that these machines can be used in both industrial and commercial applications and in home and residential applications. In addition, the treatment composition can be formulated so that it can be used in commercial and industrial laundry washing machines and residential laundry washing machines that are in common use, and are computer programmable, without modification.

In some embodiments, the methods are suitable for use in washer-extractor machines. In an embodiment, the methods can be applied in a front loading horizontal axis washer. In another embodiment, the methods can be applied in a top loading washer. Laundry washing machines that can be used according to the methods can be characterized as horizontal axis or vertical axis washers depending upon the axis of rotation.

In other embodiments, tunnel washers and continuous bath washers can be utilized according to the methods. A tunnel washer consists of several compartments that are arranged in a tunnel-like construction. The laundry remains in each compartment for a certain time and then is transported to the next compartment by top-transfer or bottom-transfer. Each compartment can be connected to a dosing unit that allows the addition of one or more laundry components. In this way, the cleaning, sanitizing and/or disinfecting composition of the first component and the bleaching, sanitizing and/or disinfecting composition of the second component, as well as other chemicals for the treatment of the laundry cam be added independently into various compartments of the tunnel washer.

Laundry/Textiles

Any of a variety of textile articles can benefit from being washed according to the present method. Suitable textile articles include those from hospitality, health care, industrial, and food service facilities. In an embodiment, the textile cleaned by the present is a white textile article or a colored synthetic (e.g., polyester) textile article. In an embodiment, the textile is a white cotton textile article. In an embodiment the textile articles are from a health care facility. That is, the textiles are textile articles employed in health care. Such health care textile articles include, for example, a sheet, a towel, a patient gown, a bed spread, an incontinence pad, an operating room linen, a scrub, a wash cloth, a pillow case, or a mixture thereof.

Methods of Antimicrobial Disinfection and Bleaching Laundry

The laundry treatment methods can provide for antimicrobial and bleaching treatment and employ a peroxyformic acid composition. The peroxyformic acid composition comprises peroxyformic acid, formic acid and hydrogen peroxide. Additional components can be included in the peroxyformic acid composition. The peroxyformic acid composition can be provided in the form of a concentrate that is diluted with water to provide a use solution. The use solution can be used for washing articles such as laundry.

Figure 2:
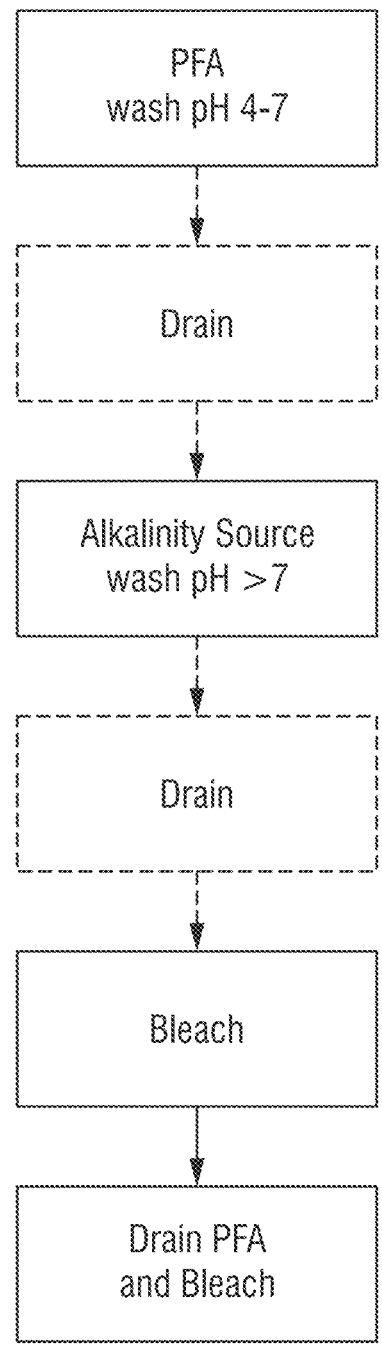
FIGS. 2-4 show exemplary diagrams of the methods of employing a peroxyformic acid composition in a laundry washing cycle in combination with a chlorine bleach composition.
Figure 3:
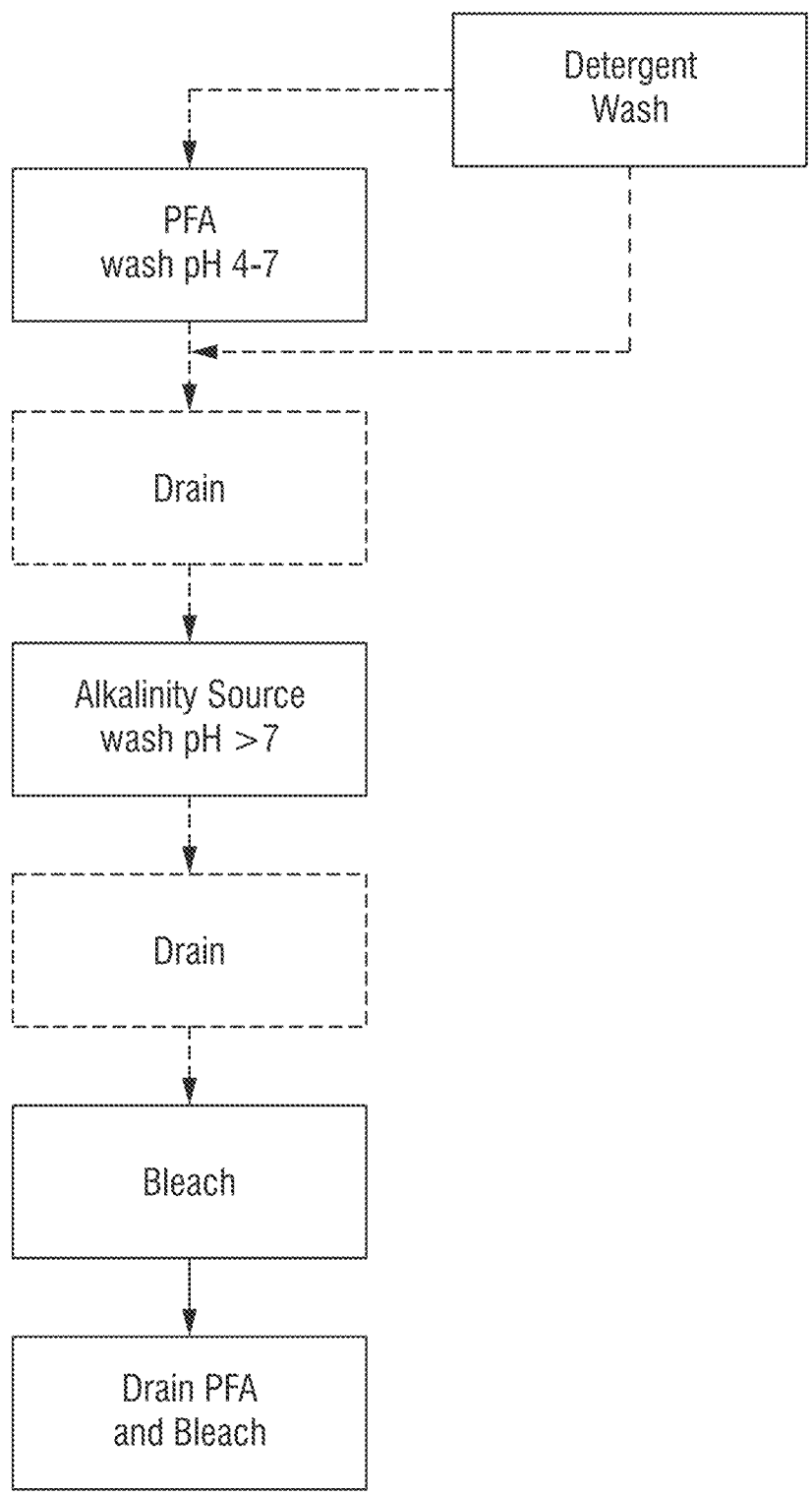
Figure 4:
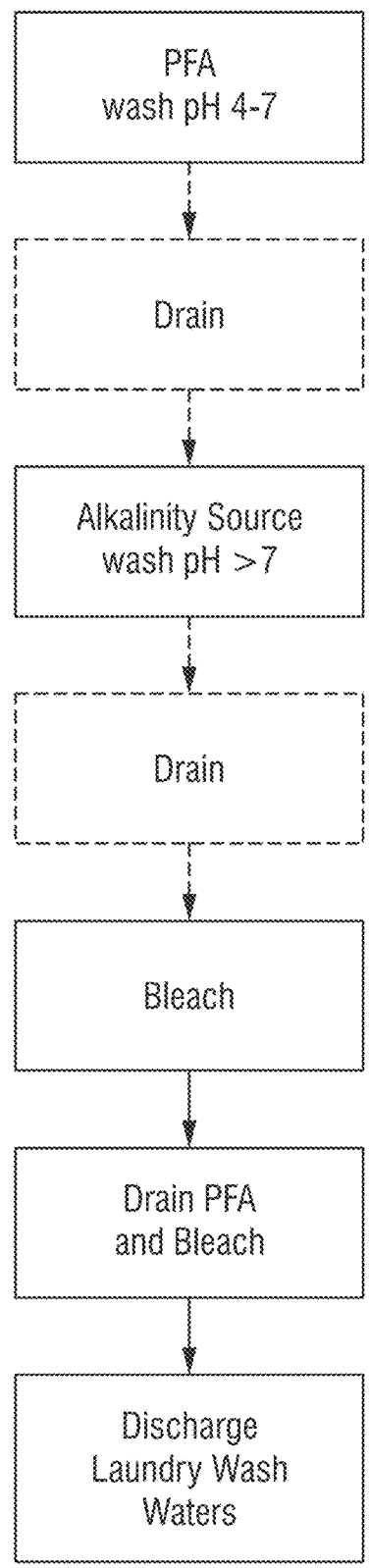

Beneficially, the method of antimicrobial sanitizing and/or disinfecting and bleaching laundry with a peroxyformic acid composition followed by a bleaching component disinfects and/or sanitizes the laundry and removes bacteria, viruses or other contaminants (including for example as depicted in FIG. 2). The dosing of a bleaching component can either following the addition of an alkalinity source to increase the pH of the wash (as shown in FIGS. 2-4) or could be fed into the washing machine simultaneously with the alkalinity source. The simultaneous dosing of the bleaching component and alkalinity source is not depicted in FIGS. 2-4 but represents an alternative embodiment of the methods. Beneficially, according to such an aspect, the sanitizing and/or disinfecting kills the bacteria, viruses or other contaminants before any wash waters are discharged from the laundry washing machine (including for example as depicted in FIG. 4). However, in other aspects, the method of antimicrobial sanitizing and/or disinfecting and bleaching laundry can follow an initial washing step for the laundry, such as employing a detergent composition (including for example as depicted in FIG. 3). In the various depicted embodiments, optional draining steps may be employed after the dosing of the peroxyformic acid composition, after the dosing of the alkalinity source, and/or after the simultaneous dosing of the alkalinity source and the bleach component.

The method for treating laundry can be provided as part of an overall method for cleaning laundry. That is, as part of a laundry cleaning operation, the laundry can be treated with an antimicrobial and bleaching composition to provide antimicrobial and bleaching properties. The antimicrobial properties can be characterized as sanitizing when there is a substantial reduction of bacteria, fungi, spores, and other microorganisms or microorganism generating materials on a surface being treated to provide a sanitized surface. For laundry applications a substantial reduction refers to a reduction of at least three orders of magnitude and can be referred to as a three-$log_{10}$ reduction. Preferably, the reduction can be at least four orders of magnitude, and more preferably at least five orders of magnitude.

The method for treating laundry refers to the treatment of laundry with the peroxyformic acid composition as substantially shown and depicted in FIGS. 2-4. The methods include the steps as depicted in FIG. 2 for washing the laundry with a peroxyformic acid composition at a pH range from about 4 to about 7 for antimicrobial effects, followed by adding an alkalinity source to the washing machine to increase the pH to at least about 7 for bleach efficacy when the bleach component is thereafter applied to the wash, and thereafter draining the peroxyformic acid composition and the chlorine bleach component from the laundry.

The conditions for employing the peroxyformic acid composition include contacting the laundry with the peroxyformic acid composition at a pH from about 2 to about 10, from about 2 to about 9, from about 2 to about 8, from about 4 to about 9, from about 4 to about 8, from about 5 to about 8, or preferably less than about 7 to provide a pH that favors the antimicrobial treatment. As depicted in FIG. 2 a preferred pH range of about 4 to about 7 is depicted; however the pH ranges disclosed herein can be applied to a method of for treating laundry and the figure is not intended to limit the scope of the disclosure and/or claims. In some embodiments a pH of at least 4 is preferred to ensure an acidic pH does not damage the fabric of the laundry and less than about 7 for micro efficacy of the peroxyformic acid. In preferred embodiments, the treatment of laundry with the peroxyformic acid composition is at a pH from about 4 to about 7, or more preferably form about 5 to about 7, and most preferably form about 6 to about 7. In an aspect, the method of applying the peroxyformic acid composition to the laundry in the laundry washing machine is for a period of time of at least a few minutes, or about 3 to about 15 minutes, or for about 5 to about 10 minutes. In general, it is expected that sufficient antimicrobial effect can occur at a time of between about 1 and about 20 minutes, at a time of between about 2 and about 15 minutes, and a time of between about 3 minutes and about 10 minutes.

Thereafter, the method for treating laundry includes the step of adding an alkalinity source to the washing machine to increase the pH range to at least about 7, at least above 8, above 9, and preferably above 10, or still further from about 10 to about 11, or at least about 11. Any suitable alkalinity source can be employed according to the methods. Exemplary alkalinity sources include at least one of alkali metal hydroxide, alkali metal silicate, alkali metal carbonate or other base components. As a skilled artisan will appreciate, the increase in pH by the alkalinity source is temperature dependent. A lower temperature range employed in the antimicrobial and/or bleaching step will require a lower pH adjustment.

Thereafter, the method for treating laundry includes the providing of a bleaching component at an alkaline pH, at a pH greater than about 7, preferably at a pH from about 9 to about 13, or preferably at a pH from about 10 to about 13 to provide a pH that favors the bleaching treatment. As one skilled in the art will appreciate the pH for the bleaching component is also driven by temperature of the application to the laundry, therefore, if a lower temperature (such as below about 120° F., or below about 100° F. is employed a pH lower than 9-10 can be employed as well). The bleach solution is applied to the laundry in the laundry washing machine for about 3 to about 15 minutes, or for about 5 to about 10 minutes. In general, it is expected that sufficient bleaching can occur at a time of between about 1 and about 20 minutes, at a time of between about 2 and about 15 minutes, and a time of between about 3 minutes and about 10 minutes. The bleaching component can be added in an amount between about 50 ppm and about 100 ppm, or between about 50 ppm and about 500 ppm, or between about 50 ppm and about 1000 ppm. As a skilled artisan will appreciate, the bleaching step is concentration, pH, temperature, and time dependent step in the methods pursuant to the methods.

Beneficially, the methods of using peroxyformic acid before a bleaching step are suitable for use at low temperature antimicrobial disinfection. In an aspect, low temperatures for methods disclosed herein include temperatures of at least about 30° C. As used herein, the phrase "low temperature" can refer to a temperature of about 50° C. at the most. Beneficially, the lower the temperature of the antimicrobial step of the methods, the more advantageous the peroxyformic acid compositions are in comparison to other biocides, including other peroxycarboxylic acids. It an embodiment temperatures as low as C can be employed. In an aspect, ambient temperatures can be employed. However, one could employ high temperatures above 120° F., such as 140° F. or above.

The method for treating laundry can optionally include a detergent step. In an embodiment the detergent step precedes the antimicrobial peroxyformic acid composition (as depicted in FIG. 3). In another embodiment the detergent step follows the antimicrobial peroxyformic acid composition (as depicted in FIG. 3). An optionally drain step can be included before the dosing of a detergent step and/or after a detergent step. A detergent step comprises providing a detergent use solution at an alkaline pH, preferably at a pH from about 9 to about 13. In general, it is expected that an alkaline wash refers to a wash that takes place at a pH at between about 7 and about 13, and can include a pH of between about 8 and about 12. The detergent use solution is applied to the laundry in the laundry washing machine for about 3 to about 15 minutes, or for about 5 to about 10 minutes. The detergent use solution can be a neutral to highly alkaline detergent use solution. As referred to herein detergent use solutions include an alkalinity agent and a cleaning agent, which can include any component providing soil removal properties when dispersed or dissolved in an aqueous solution and applied to a substrate for removal of soil therefrom. Exemplary alkalinity agents include at least one of alkali metal hydroxide, alkali metal silicate, alkali metal carbonate or other base components. The detergent use solution can further include any one or more of surfactants, chelants, builders, polymers, water conditioning agents, enzymes, or other functional ingredients as the cleaning agent. In an aspect, the detergent step and/or alkalinity step can be simultaneously dosed with the bleaching component. In a further aspect, a drain step can precede and/or follow the detergent step, alkalinity step and/or bleaching step. As referred to herein, a draining step can optionally include an initial or subsequent rinsing step.

The method for treating laundry can optionally include the additional step of rinsing the peroxyformic acid composition, and the bleaching component from the laundry. In an aspect, the laundry is rinsed with water in the laundry washing machine for at least about 1 minute, or from about 1 minute to about 6 minutes. Beneficially, according to the methods the peroxyformic acid composition degrades into its inert components and therefore does not remain in the laundry solution as long as conventional biocides and/or other sanitizing or antimicrobial components.

The method for treating laundry can optionally include the additional step of adding an adjuvant use solution comprising at least one of souring agents, fabric softening agents, starch, anti-wrinkle agents, sizing agents, colorfastness agents, oil and water repellant agents, water conditioning agents, iron controlling agents, water threshold agents, soil releasing agents, soil shielding agents, optical brightening agents, fragrances, and mixtures thereof. In an aspect, the addition of the adjuvant use solution can be added at any step of the process to enhancing the cleaning and/or the antimicrobial efficacy, sanitizing and/or disinfecting and bleaching of the laundry. In an aspect, the adjuvant use solution is applied to the laundry in the laundry washing machine at a pH from about 5 to about 8 for about 1 to about 6 minutes. Although not depicted in the figures, in a preferred embodiment, a finishing or sour step is added after the draining of the peroxyformic acid and bleach compositions. In such embodiments, any number of draining and/or rinsing steps can be precede the finishing or sour step.

Additional Methods of Antimicrobial Disinfection and Bleaching

The treatment methods can be applied to other applications besides laundry where there is a need for an antimicrobial and bleaching treatment employing a peroxyformic acid composition. The peroxyformic acid composition can be provided in the form of a concentrate that is diluted with water to provide a use solution for a treatment application. The use solution can be used for water treatment and/or paper processing and/or treatment. Beneficially, the method of antimicrobial sanitizing and/or disinfecting and bleaching water and/or paper sources with a peroxyformic acid composition followed by a bleaching component disinfects the surface or medium and remove bacteria, viruses or other contaminants.

Peroxyformic Acid Compositions

The peroxyformic acid compositions provide the antimicrobial and bleaching efficacy according to the methods. It is desirable to provide the treatment use composition at a pH that favors antimicrobial and bleaching treatment first at a relatively low pH to effect a desired level of antimicrobial treatment and the bleaching at a higher pH (as achieved by dosing the alkalinity source) in order to effect the desired level of bleaching through use of the bleaching component which is effective for bleaching without damaging the laundry (e.g. textile substrates) at alkaline pH. As one skilled in the art understands the use of bleaching component at a more acidic pH can cause damage to the laundry and can also release Chlorine gas at too low of a pH.

The peroxyformic acid compositions can include equilibrium or non-equilibrium compositions comprising, consisting of and/or consisting essentially of peroxyformic acid, formic acid, hydrogen peroxide and water. Additional components can be included in the peroxyformic acid composition. A peroxyformic acid composition can be provided to a wash machine as a concentrate or a use solution. A peroxyformic acid composition can be generated onsite or off-site and provided to a wash machine.

In some embodiments, the peroxyformic acid compositions include a ratio of peroxyformic acid to hydrogen peroxide having a lower ratio of hydrogen peroxide in comparison to other peroxycarboxylic acids. In an aspect, the ratio of peroxyformic acid to hydrogen peroxide is at least 4:1, at least 5:1, at least 6:1, at least 7:1, at least 8:1, at least 9:1, at least 10:1, at least 11:1, at least 12:1, at least 13:1, at least 14:1, at least 15:1, at least 16:1, at least 17:1, at least 18:1, at least 19:1, at least 20:1, at least 21:1, at least 22:1, at least 23:1, at least 24:1, at least 25:1, at least 26:1, at least 27:1, at least 28:1, at least 29:1, or at least 30:1. This is distinct from various other peroxycarboxylic acids, such as peroxyacetic acid having a ratio of peroxycarboxylic acid to hydrogen peroxide of about 1:1 to about 1.5:1. Beneficially, as disclosed according to the methods the low concentration of hydrogen peroxide according to embodiments of the methods provides an antimicrobial sanitizing and/or disinfecting step with low amounts of active oxygen component to avoid negative interaction with the bleaching component. As one skilled in the art will appreciate based on the disclosure set forth herein, the stoichiometric relationship between oxygen from the hydrogen peroxide or the degraded peroxyformic acid of the composition, neutralizes the chlorine in a bleach component. Beneficially as provided by the methods, the less oxygen available from the peroxyformic acid composition (i.e. hydrogen peroxide) the less chlorine from the bleaching component will be negatively impacted or removed from solution, thereby positively impacting bleaching efficacy when combined with the peroxyformic acid composition.

In an aspect, the peroxyformic acid composition is provided at an actives level from about 5 ppm to about 200 ppm, from about 5 ppm to about 100 ppm, from about 5 ppm to about 80 ppm, from about 10 ppm to about 80 ppm, or preferably from about 20 ppm to about 80 ppm. In more preferred embodiments, the peroxyformic acid composition is provided at an actives level from about 5 ppm to about 80 ppm, or from about 5 ppm to about 40 ppm. In a beneficial aspect of the methods described herein, the peroxyformic acid composition can be dosed at a lower active level in comparison to other peroxycarboxylic acid compositions, such as peroxyacetic acid having a propensity to knock-out the bleaching composition employed in the methods.

Peroxyformic acid compositions can be generated through reaction of an ester of a polyhydric alcohol and formic acid and hydrogen peroxide or a substance that generates hydrogen peroxide when in contact with a liquid, as disclosed in U.S. Pat. No. 9,518,013, which is incorporated by reference. Peroxyformic acid compositions can also be generated through a reaction of formic acid and hydrogen peroxide or a substance that generates hydrogen peroxide when in contact with a liquid, as disclosed in U.S. Patent Publication No. 2016/0176814, which is incorporated by reference. Various reactions for generating peroxyformic acid (alone or in combination with additional peracids) can be achieved through use of on-site generators, including those disclosed in U.S. Pat. Nos. 8,858,895 and 9,192,909, and U.S. Patent Publication No. 2017/0064949, which is incorporated by reference.

Peroxyformic Acid Generated with Formic Acid

Peroxyformic acid compositions can be generated through reaction of formic acid and hydrogen peroxide or a substance that generates hydrogen peroxide when in contact with a liquid. A method for forming peroxyformic acid comprises contacting formic acid with hydrogen peroxide to form a resulting aqueous composition that comprises a peracid that comprises peroxyformic acid, wherein before said contacting, the ratio between the concentration of said formic acid (w/v) and the concentration of said hydrogen peroxide (w/v) is about 2 or higher, and the ratio between the concentration of said peracid (w/w) and the concentration of hydrogen peroxide (w/w) in said formed resulting aqueous composition reaches about 2 or higher at least within 4 hours, or preferably 2 hours of said contacting. The formic acid can be provided in any suitable way. In some embodiments, before the contacting step, the formic acid can be provided in a composition that comprises formic acid, e.g., an aqueous solution that comprises formic acid. In other embodiments, before the contacting step, the formic acid can be provided in a composition that comprises a substance that generates formic acid upon contact with an aqueous composition. Any suitable substance that generates formic acid can be used in the present methods. The substance can be a salt of formate, e.g., a sodium or ammonium salt of formate, or an ester of formate. Exemplary esters of formate include glycerol formates, pentaerythritol formates, mannitol formates, propylene glycol formates, sorbitol formates and sugar formates. Exemplary sugar formates include sucrose formates, dextrin formates, maltodextrin formates, and starch formates. In some embodiments the formates may be provided in a solid composition, such as a starch formate.

The hydrogen peroxide used in the present methods can be provided in any suitable way. In some embodiments, before the contacting step, the hydrogen peroxide can be provided in a composition that comprises hydrogen peroxide, e.g., an aqueous solution that comprises hydrogen peroxide. In other embodiments, before the contacting step, the hydrogen peroxide can be provided in a composition that comprises a substance that generates hydrogen peroxide upon contact with an aqueous composition. Any suitable substance that generates hydrogen peroxide can be sued in the present methods. The substance can comprise a precursor of hydrogen peroxide. Any suitable precursor of hydrogen peroxide can be used in the present methods. For example, the precursor of hydrogen peroxide can be sodium percarbonate, sodium perborate, urea hydrogen peroxide, or PVP-hydrogen peroxide.

In some embodiments, formic acid provided in a first aqueous composition is contacted with hydrogen peroxide provided in a second aqueous composition to form peroxyformic acid in the resulting aqueous composition. In other embodiments, formic acid provided in a first aqueous composition is contacted with a substance that generates hydrogen peroxide upon contact with an aqueous composition provided in a second solid composition to form peroxyformic acid in the resulting aqueous composition. In still other embodiments, a substance that generates formic acid upon contact with an aqueous composition provided in a first solid composition is contacted with hydrogen peroxide provided in a second aqueous composition to form peroxyformic acid in the resulting aqueous composition. In yet other embodiments, a substance that generates formic acid upon contact with an aqueous composition provided in a first solid composition and a substance that generates hydrogen peroxide upon contact with an aqueous composition provided in a second solid composition are contacted with a third aqueous composition to form peroxyformic acid in the resulting aqueous composition. In yet other embodiments, a substance that generates formic acid upon contact with an aqueous composition and a substance that generates hydrogen peroxide upon contact with an aqueous composition are provided in a first solid composition, and the first solid composition is contacted with a second aqueous composition to form peroxyformic acid in the resulting aqueous composition. The resulting aqueous composition that comprises a peracid that comprises peroxyformic acid can be any suitable types of aqueous compositions. For example, the resulting aqueous composition can be an aqueous solution. In another example, the resulting aqueous composition can be an aqueous suspension.

Before the contacting step, the ratio between the concentration of the formic acid (w/v) and the concentration of the hydrogen peroxide (w/v) can be in any suitable range. In some embodiments, before the contacting, the ratio between the concentration of the formic acid (w/v) and the concentration of the hydrogen peroxide (w/v) can be from about 2 to about 100, e.g., about 2-3, 3-4, 4-5, 5-6, 6-7, 7-8, 8-9, 9-10, 10-15, 15-20, 20-25, 25-30, 30-35, 35-40, 40-45 or 45-50 or greater from about 50-100. The ratio between the concentration of the peracid (w/w) and the concentration of hydrogen peroxide (w/w) in the formed aqueous composition can reach any suitable range. In some embodiments, the ratio between the concentration of the peracid (w/w) and the concentration of hydrogen peroxide (w/w) in the formed aqueous composition can reach, within about 4 hours, or preferably 2 hours of the contacting, from about 2 to about 1,500, e.g., about 2-3, 3-4, 4-5, 5-6, 6-7, 7-8, 8-9, 9-10, 10-15, 15-20, 20-25, 25-30, 30-35, 35-40, 40-45, 45-50, 50-60, 60-70, 70-80, 80-90, 90-100, 100-200, 200-300, 300-400, 400-500, 500-600, 600-700, 700-800, 800-900, 900-1,000, 1,000-1,100, 1,100-1,200, 1,200-1,300, 1,300-1,400, or 1,400-1,500. In other embodiments, the ratio between the concentration of the peracid (w/w) and the concentration of hydrogen peroxide (w/w) in the formed aqueous composition reaches at least about 10 within about 30 minutes of the contacting, preferably at least about 10-40 within about 30 minutes of the contacting.

The formed aqueous composition can comprise any suitable concentration of hydrogen peroxide. In some embodiments, the formed aqueous composition can comprise about 5% (w/w) or less hydrogen peroxide, e.g., about 5% (w/w), 4.5% (w/w), 4% (w/w), 3.5% (w/w), 3% (w/w), 2.5% (w/w), 2% (w/w), 1.5% (w/w), 1% (w/w), 0.9% (w/w), 0.8% (w/w), 0.7% (w/w), 0.6% (w/w), 0.5% (w/w), 0.4% (w/w), 0.3% (w/w), 0.2% (w/w), 0.1% (w/w), 0.05% (w/w), 0.01% (w/w), 0.005% (w/w), or 0.001% (w/w) of hydrogen peroxide. In other embodiments, the formed aqueous composition reaches about 2% (w/w) or less hydrogen peroxide within at least about 4 hours, or preferably 2 hours of the contacting. In still other embodiments, the formed aqueous composition reaches about 1% (w/w) or less hydrogen peroxide within at least about 1 hour of the contacting. In yet other embodiments, the formed aqueous composition reaches about 0% (w/w) to about 0.001% (w/w) hydrogen peroxide and maintains about 0% (w/w) to about 0.001% (w/w) hydrogen peroxide for at least 1 hour.

The present methods can be conducted in the presence of a catalyst. Any suitable catalyst can be used in the present methods. In some embodiments, the catalyst can be a mineral acid, e.g., sulfuric acid, methanesulfonic acid, nitric acid, phosphoric acid, pyrophosphoric acid, polyphosphoric acid or phosphonic acid. The present methods can also be conducted in the presence of a cation acid exchange resin system. Any suitable cation acid exchange resin system can be used in the present methods. In some embodiments, the cation acid exchange resin system is a strong cation acid exchange resin system. In other embodiments, the acid exchange resin system is sulfonic acid exchange resin, e.g., commercially-available as Dowex M-31 or Nafion.

The resulting aqueous composition can comprise a stabilizing agent for the peracid. Any suitable stabilizing agents can be used in the present methods. Exemplary stabilizing agents include a phosphonate salt(s) and/or a heterocyclic dicarboxylic acid, e.g., dipicolinic acid.

The present methods can further comprise a step of reducing the concentration of the hydrogen peroxide in the resulting aqueous composition. The concentration of the hydrogen peroxide in the resulting aqueous composition can be reduced using any suitable methods. For example, the concentration of the hydrogen peroxide in the resulting aqueous composition can be reduced using a catalase or a peroxidase.

Peroxyformic Acid Generated with Esters of a Polyhdric Alcohol and Formic Acid

Peroxyformic acid compositions can be generated through reaction of an ester of a polyhydric alcohol and formic acid and hydrogen peroxide or a substance that generates hydrogen peroxide when in contact with a liquid. Peroxyformic acid forming compositions according to the methods comprise: a) a first reagent that comprises an ester of a polyhydric alcohol and formic acid, and b) a second reagent that comprises hydrogen peroxide or that comprises a substance that generates hydrogen peroxide when in contact with a liquid, wherein 1) said first reagent and said second reagent are kept separately prior to use, and when it is time to generate peroxyformic acid, said first reagent and said second reagent are configured to be contacted with each other to form a liquid that comprises peroxyformic acid and has a pH below about 11, and pH of the formed liquid becomes about 8 or lower within about 1 minute after the contact between said first reagent and said second reagent; or 2) said second reagent comprises a substance that generates hydrogen peroxide when in contact with a liquid, said first reagent and said second reagent are comprised in a solid composition, and when it is time to generate peroxyformic acid, said solid composition is configured to be contacted with a liquid to form a liquid that comprises peroxyformic acid and has a pH below about 11, and pH of the formed liquid becomes about 8 or lower within about 1 minute after the contact between said solid composition and said liquid.

The present peroxyformic acid forming compositions can comprise any suitable ester of a polyhydric alcohol and formic acid. Typically, a polyhydric alcohol refers to a molecule with two or more hydroxyl (—OH) groups. An ester of a polyhydric alcohol and formic acid refers to an ester formed between a polyhydric alcohol and formic acid. Esters as referred to herein are considered 'water-less' systems as no additional water is added to the reaction. In some embodiments, the present peroxyformic acid forming compositions comprise glycerol formates, pentaerythritol formates, mannitol formates, propylene glycol formates, sorbitol formates and sugar formates. The present peroxyformic acid forming compositions can comprise any suitable sugar formates, e.g., sucrose formates, dextrin formates, maltodextrin formates, or starch formates.

In a preferred embodiment, a liquid reaction employs glycerol formates, pentaerythritol formates, mannitol formates, or propylene glycol formates. In a still further preferred embodiment, a liquid reaction employs glycerol formates. Beneficially, the glycerol formates rapidly undergo hydrolysis for peroxyformic acid generation according to the methods. In an aspect, the precursors provided do not include additional water added into the system which would negatively interfere with the kinetics of the reaction between the ester of a polyhydric alcohol and formic acid and hydrogen peroxide. In an aspect, the premixes and the peroxyformic acid forming composition do not add free water into the systems, which would negatively interfere with the ester, e.g. glycerol formates.

In a preferred embodiment, a solid reaction employs sugar formates e.g., sucrose formates, dextrin formates, maltodextrin formates, or starch formates. In a still further preferred embodiment, a solid reaction employs starch formates.

The present peroxyformic acid forming compositions can comprise a use solution or a concentrate of the ester of a polyhydric alcohol and formic acid. In some aspects, the methods generate a peroxyformic acid through a concentrate reaction of the ester of a polyhydric alcohol and formic acid. In other aspects, the methods generate a peroxyformic acid through a diluted use solution reaction of the ester of a polyhydric alcohol and formic acid.

The first or second reagent can have any suitable pH range in the present peroxyformic acid forming compositions. For example, the first or second reagent can have a pH below about 11, or from about −2 to about 11, or from about 0 to about 11, e.g., about −2 to about −1, −2 to about 0, 0-1, 0-2, 0-3, 0-4, 0-5, 0-6, 0-7, 0-8, 0-9, 0-10, 0-11, 1-2, 1-3, 1-4, 1-5, 1-6, 1-7, 1-8, 1-9, 1-10, 1-11, 2-3, 2-4, 2-5, 2-6, 2-7, 2-8, 2-9, 2-10, 2-11, 3-4, 3-5, 3-6, 3-7, 3-8, 3-9, 3-10, 3-11, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 6-7, 7-8, 7-9, 7-10, 7-11, 8-9, 8-10, 8-11, 9-10, 9-11, 10-11, or at about −2, −1, 0, 1, 2, 3, 4, 5, 6, 7, 8, 9, 10 or 11. In some embodiments, the first or second reagent has a pH ranging from about 5 to about 10, e.g., about 5-6, 5-7, 5-8, 5-9, 5-10, 6-7, 6-8, 6-9, 6-10, 7-8, 7-9, 7-10, 8-9, 8-10, or 9-10. In other embodiments, the first or second reagent has a pH at about 9.

The first reagent and the second reagent can be configured to be contacted with each other to form a liquid, e.g., a solution, that comprises peroxyformic acid and has any suitable pH, including a pH below about 11, or from about −2 to about 11, or from about 0 to about 11, e.g., about −2 to about −1, −2 to about 0, 0-1, 0-2, 0-3, 0-4, 0-5, 0-6, 0-7, 0-8, 0-9, 0-10, 0-11, 1-2, 1-3, 1-4, 1-5, 1-6, 1-7, 1-8, 1-9, 1-10, 1-11, 2-3, 2-4, 2-5, 2-6, 2-7, 2-8, 2-9, 2-10, 2-11, 3-4, 3-5, 3-6, 3-7, 3-8, 3-9, 3-10, 3-11, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 6-7, 7-8, 7-9, 7-10, 7-11, 8-9, 8-10, 8-11, 9-10, 9-11, 10-11, or at about −2, −1, 0, 1, 2, 3, 4, 5, 6, 7, 8, 9, 10 or 11. In some embodiments, the first reagent and the second reagent are configured to be contacted with each other to form a liquid, e.g., a solution, that comprises peroxyformic acid and has a pH ranging from about −2 to about 11, 0 to about 10, or 5 to about 10, e.g., about −2-0, 0-1, 1-2, 2-3, 3-4, 4-5, 5-6, 5-7, 5-8, 5-9, 5-10, 6-7, 6-8, 6-9, 6-10, 7-8, 7-9, 7-10, 8-9, 8-10, 9-10, or 10-11. In other embodiments, the first reagent and the second reagent are configured to be contacted with each other to form a liquid, e.g., a solution, that comprises peroxyformic acid and has a pH at about 9. In a preferred aspect, the formed liquid, e.g., a solution, that comprises peroxyformic acid and has a pH near neutral, from about 6-7.

The pH of the formed liquid can become about 8 or lower within about 1 minute after the contact between the first reagent and the second reagent or after the contact between the solid composition and the liquid. In some embodiments, the pH of the formed liquid can become about 8 or lower within about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds after the contact between the first reagent and the second reagent or after the contact between the solid composition and the liquid. In other embodiments, the pH of the formed liquid comprising peroxyformic acid becomes about 8 or lower within about 1 minute or less. In an aspect, the pH of the formed liquid comprising peroxyformic acid becomes about 8 or lower within about 45 seconds or less, 40 seconds or less, 35 seconds or less, 30 seconds or less, 25 seconds or less, 20 seconds or less, 15 seconds or less, 10 seconds or less, or 5 seconds or less. In an aspect, the pH of the formed liquid comprising peroxyformic acid becomes about 8 or lower near instantaneously. In other embodiments, the pH of the formed liquid can become about lower than −2, −1, 0, 1, 2, 3, 4, 5, 6, 7, or 8 within about 1 minute after the contact between the first reagent and the second reagent or after the contact between the solid composition and the liquid.

The liquid that comprises peroxyformic acid can maintain the pH ranging from about −2 to about 8, or from about 0 to about 8 for any suitable time after the contact between the first reagent and the second reagent, or after the contact between the composition and a liquid. In some embodiments, the liquid that comprises peroxyformic acid maintains the pH ranging from about −2 to about 8, or from about 0 to about 8 from about 1 second to about 10 hours after the contact between the first reagent and the second reagent or after the contact between the composition and a liquid. For example, the liquid that comprises peroxyformic acid can maintain the pH at about −2, −1, 0, 1, 2, 3, 4, 5, 6, 7, or 8 from about 1 second to about 10 hours after the contact between the first reagent and the second reagent or after the contact between the composition and a liquid. In another example, the liquid that comprises peroxyformic acid can maintain the pH ranging from about 0 to about 8 for about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours. In a preferred aspect, the formed liquid, e.g., a solution, that comprises peroxyformic acid and has a pH near neutral, from about 6-7 in a use solution.

In some embodiments, the first reagent and the second reagent are configured to be contacted with each other to form a solution that comprises peroxyformic acid and has a pH ranging from about 4 to about 8 or 9, e.g., about 4-5, 5-6, 6-7, 7-8, or 8-9. In a preferred aspect, the formed liquid, e.g., a solution, that comprises peroxyformic acid and has a pH near neutral, from about 6-7 in a use solution. In one example, the first reagent and the second reagent are configured to be contacted with each other to form a solution that comprises peroxyformic acid and has a pH ranging from about 6 to about 8 or 9. The first reagent and the second reagent can be configured to be contacted with each other to form a solution that comprises peroxyformic acid and has a pH ranging from about 4 to about 8 or 9, and the solution can maintain the pH range for any suitable amount of time, e.g., from about 1 minute to about 24 hours. For example, the solution can maintain the pH range from about 4 to about 8 or 9 for at least about 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours.

In other embodiments, the solid composition is configured to be contacted with a liquid to form a solution that comprises peroxyformic acid and has a pH ranging from about 4 to about 8 or 9, e.g., about 4-5, 5-6, 6-7, 7-8, or 8-9. In one example, the solid composition is configured to be contacted with a liquid to form a solution that comprises peroxyformic acid and has a pH ranging from about 6 to about 8 or 9. The solid composition is configured to be contacted with a liquid to form a solution that comprises peroxyformic acid and has a pH ranging from about 4 to about 8 or 9, and the solution can maintain the pH range for any suitable amount of time, e.g., from about 1 minute to about 24 hours. For example, the solution can maintain the pH range from about 4 to about 8 or 9 for at least about 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours. In a preferred aspect, the formed liquid, e.g., a solution, that comprises peroxyformic acid and has a pH near neutral, from about 6-7 in a use solution.

The first reagent and the second reagent can be configured to be contacted with each other to form a liquid, e.g., a solution, that comprises peroxyformic acid under any suitable conditions or temperature. In some embodiments, the first reagent and the second reagent are configured to be contacted with each other to form a liquid, e.g., a solution, that comprises peroxyformic acid under ambient conditions. In other embodiments, the first reagent and the second reagent are configured to be contacted with each other to form a liquid, e.g., a solution, that comprises peroxyformic acid at a temperature ranging from about −2° C. to about 60° C., 0° C. to about 60° C., or 4° C. to about 60° C., e.g., about −2° C.-0° C., 0° C.-4° C., 4° C.-5° C., 4° C.-5° C., 5° C.-10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., or 55° C.-60° C. In still other embodiments, the first reagent and the second reagent are configured to be contacted with each other to form a liquid, e.g., a solution, that comprises peroxyformic acid at a temperature at about 4° C. or lower than 4° C., e.g., at about 3° C., 2° C., 1° C., 0° C., or lower than 0° C.

The solid composition can be configured to be contacted with a liquid to form a liquid, e.g., a solution, that comprises peroxyformic acid under any suitable conditions or temperature. In some embodiments, the solid composition can be configured to be contacted with a liquid to form a liquid, e.g., a solution, that comprises peroxyformic acid under ambient conditions. In other embodiments, the solid composition can be configured to be contacted with a liquid to form a liquid, e.g., a solution, that comprises peroxyformic acid at a temperature ranging from about −2° C. to about 60° C., 0° C. to about 60° C., or 4° C. to about 60° C., e.g., about −2° C.-0° C., 0° C.-4° C., 4° C.-5° C., 4° C.-5° C., 5° C.-10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., or 55° C.-60° C. In still other embodiments, the solid composition can be configured to be contacted with a liquid to form a liquid, e.g., a solution, that comprises peroxyformic acid at a temperature at about 4° C. or lower than 4° C., e.g., at about 3° C., 2° C., 1° C., 0° C., or lower than 0° C.

The present peroxyformic acid forming compositions can further comprise a catalyst (e.g. mineral acid) or an enzyme that catalyzes formation of peroxyformic acid from the ester of a polyhydric alcohol and formic acid, and hydrogen peroxide. The present peroxyformic acid forming compositions can comprise any suitable catalyst, e.g., a strong mineral acid, or enzyme, e.g., a perhydrolytic enzyme, lipase, coronase, termanyl or esperease. The catalyst or an enzyme can be comprised in any suitable part of the present peroxyformic acid forming compositions. In some embodiments, the first reagent comprises the catalyst or enzyme. In other embodiments, the second reagent comprises the catalyst or enzyme. In still other embodiments, the present peroxyformic acid forming compositions can further comprise a third reagent that comprises the catalyst or enzyme. In yet other embodiments, the solid composition comprises the catalyst or enzyme.

The present peroxyformic acid forming compositions can further comprise a stabilizing agent for peroxyformic acid, a stabilizing agent for hydrogen peroxide, and/or a pH buffering agent. In an aspect the stabilizing agent(s) and/or pH buffering agents are useful in decreasing a pH of the compositions to neutral or lower pH. The present peroxyformic acid forming compositions can comprise any suitable stabilizing agent. Exemplary stabilizing agents include a phosphonate salt(s) and/or a heterocyclic dicarboxylic acid, e.g., dipicolinic acid. In some embodiments, the stabilizing agent is pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts. In other embodiments, the present peroxyformic acid forming compositions comprise two or more stabilizing agents, e.g., HEDP and 2,6-pyridinedicarboxylic acid (DPA). The stabilizing agent(s) can be comprised in any suitable part of the present peroxyformic acid forming compositions. In some embodiments, the first reagent comprises a stabilizing agent for peroxyformic acid and/or a pH buffering agent. In other embodiments, the second reagent comprises a stabilizing agent for hydrogen peroxide. In still other embodiments, the present peroxyformic acid forming compositions can further comprise a third reagent that comprises a stabilizing agent for peroxyformic acid, a stabilizing agent for hydrogen peroxide, and/or a pH buffering agent. In yet other embodiments, the solid composition comprises a stabilizing agent for peroxyformic acid, a stabilizing agent for hydrogen peroxide, and/or a pH buffering agent.

The present peroxyformic acid forming compositions can comprise any suitable pH buffering agent. The pH buffer reagent can include any reagent that is compatible with the ester(s) in the present peroxyformic acid forming compositions. Exemplary buffer agents suitable for using with a liquid ester can be an organic amine, such as triethanol amine, imidazole, etc. Exemplary buffer agents suitable for using with a solid form of ester include a broader range of buffers, such as a carbonate salt, a phosphate salt, etc. The pH buffer reagent can be comprised in any suitable part of the present peroxyformic acid forming compositions. In some embodiments, the first reagent comprises a pH buffering agent. In other embodiments, the present peroxyformic acid forming compositions can further comprise a third reagent that comprises a pH buffering agent. In still other embodiments, the solid composition comprises a pH buffering agent.

The present peroxyformic acid forming compositions can comprise any suitable stabilizing agent for hydrogen peroxide. Exemplary stabilizing agents for hydrogen peroxide include phosphonates, heterocyclic carboxylic acids and the mixtures thereof. In some embodiments, stabilizing agents for hydrogen peroxide can be Dequest 2010, Dequest 2066, Dipicolinic acids, etc. The stabilizing agent for hydrogen peroxide can be comprised in any suitable part of the present peroxyformic acid forming compositions. In some embodiments, the second reagent comprises a stabilizing agent for hydrogen peroxide. In other embodiments, the present peroxyformic acid forming compositions can further comprise a third reagent that comprises a stabilizing agent for hydrogen peroxide. In still other embodiments, the solid composition comprises a stabilizing agent for hydrogen peroxide.

The present peroxyformic acid forming compositions can comprise any suitable concentration of an ester of a polyhydric alcohol and formic acid. For example, the first reagent of the peroxyformic acid forming composition can comprise any suitable concentration of an ester of a polyhydric alcohol and formic acid. In some embodiments, the formed liquid is a concentrate and comprises the first reagent in an amount up to about 90% of an ester of a polyhydric alcohol and formic acid. In other embodiments, the formed liquid comprises the first reagent in an amount from about 1 ppm to about 500,000 ppm of an ester of a polyhydric alcohol and formic acid, or from about 10 ppm to about 500,000 ppm of an ester of a polyhydric alcohol and formic acid. For example, the first reagent in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, 90,000-100,000 ppm, 100,000-150,000 ppm, 150,000-200,000 ppm, 200,000-250,000 ppm, 250,000-300,000 ppm, 300,000-350,000 ppm, 350,000-400,000 ppm, 400,000-450,000 ppm, or 450,000-500,000 ppm. In other embodiments, the first reagent in the formed liquid can comprise from about 50 ppm to about 40,000 ppm of an ester of a polyhydric alcohol and formic acid, e.g., 50-100, 50-500, 50-1,000, 50-1,500, 50-2,000, 50-2,500, 50-3,000, 50-3,500, 50-4,000, 50-4,500, 50-5,000, 50-10,000, 50-20,000, 50-30,000, or 50-40,000 ppm of an ester of a polyhydric alcohol and formic acid.

In another example, the solid composition of the peroxyformic acid forming composition can comprise any suitable concentration of an ester of a polyhydric alcohol and formic acid. In some embodiments, the solid composition can provide a concentrate formed liquid that comprises the first reagent in an amount up to about 90% of an ester of a polyhydric alcohol and formic acid. In other embodiments, the solid composition can provide for the formed liquid from about 10 ppm to about 500,000 ppm of an ester of a polyhydric alcohol and formic acid. For example, the solid composition can provide for the formed liquid the ester of a polyhydric alcohol and formic acid in amounts comprising from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, 90,000-100,000 ppm, 100,000-150,000 ppm, 150,000-200,000 ppm, 200,000-250,000 ppm, 250,000-300,000 ppm, 300,000-350,000 ppm, 350,000-400,000 ppm, 400,000-450,000 ppm, or 450,000-500,000 ppm. In other embodiments, the solid composition can provide for the formed liquid from about 50 ppm to about 40,000 ppm of an ester of a polyhydric alcohol and formic acid, e.g., 50-100, 50-500, 50-1,000, 50-1,500, 50-2,000, 50-2,500, 50-3,000, 50-3,500, 50-4,000, 50-4,500, 50-5,000, 50-10,000, 50-20,000, 50-30,000, or 50-40,000 ppm of an ester of a polyhydric alcohol and formic acid.

The present peroxyformic acid forming compositions can comprise any suitable concentration of hydrogen peroxide or a substance that generates hydrogen peroxide upon contact with a liquid. For example, the second reagent of the peroxyformic acid forming composition can comprise any suitable concentration of hydrogen peroxide. In some embodiments, a concentrate formed liquid comprises the second reagent in an amount up to about 10% of hydrogen peroxide. In some embodiments, the formed liquid comprises the second reagent in an amount comprising about 0.1 ppm to about 100,000 ppm of hydrogen peroxide, or about 0.1 ppm to about 100,000 ppm of hydrogen peroxide. For example, the second reagent in the formed liquid can comprise from about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, or 90,000-100,000 ppm, 100,000-150,000 ppm, 150,000-200,000 ppm, 200,000-250,000 ppm, or 250,000-300,000 ppm hydrogen peroxide. In other embodiments, the second reagent in the formed liquid comprises from about 150 ppm to about 50,000 ppm of hydrogen peroxide, e.g., about 150-200, 150-300, 150-400, 150-500, 150-600, 150-700, 150-800, 150-900, 150-1,000, 150-1,500, 150-2,000, 150-2,500, 150-3,000, 150-3,500, 150-4,000, 150-4,500, 150-5,000, 150-10,000, 50-20,000, 50-30,000, 50-40,000 or 50-50,000 ppm of hydrogen peroxide.

In some embodiments, a concentrate formed liquid comprises the second reagent in an amount up to about 10% of hydrogen peroxide. In another example, the solid composition can comprise a substance at an amount or concentration that generates from about 0.1 ppm to about 100,000 ppm of hydrogen peroxide upon contact with a liquid in the formed liquid. For example, the solid composition can comprise a substance at an amount or concentration that generates from about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, or 90,000-100,000 ppm hydrogen peroxide.

The present peroxyformic acid forming compositions can be configured to form a liquid, e.g., a solution, that comprises any suitable concentration of peroxyformic acid. For example, the first reagent and the second reagent in the present peroxyformic acid forming compositions can be configured to be contacted with each other to form a liquid and/or solid, e.g., a solution, that comprises any suitable concentration of peroxyformic acid. In some embodiments, the first reagent and the second reagent can be configured to be contacted with each other to form a liquid, e.g., a solution, that comprises from about 0.1 ppm to about 100,000 ppm of peroxyformic acid, from about 0.1 ppm to about 10,000 ppm of peroxyformic acid, or from about 0.1 ppm to about 5,000 ppm of peroxyformic acid, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm or greater of peroxyformic acid. In other embodiments, the first reagent and the second reagent can be configured to be contacted with each other to form a liquid, e.g., a solution, that comprises from about 1 ppm to about 500 ppm of peroxyformic acid, e.g., about 0.1-1 ppm, 0.1-10 ppm, 0.1-20 ppm, 0.1-30 ppm, 0.1-40 ppm, 0.1-50 ppm, 0.1-60 ppm, 0.1-70 ppm, 0.1-80 ppm, 0.1-90 ppm, 0.1-100 ppm, 0.1-150 ppm, 0.1-200 ppm, 0.1-250 ppm, 0.1-300 ppm, 0.1-350 ppm, 0.1-400 ppm, 0.1-450 ppm, 0.1-500 ppm of peroxyformic acid. In still other embodiments, the first reagent and the second reagent can be configured to be contacted with each other to form a liquid, e.g., a solution, that comprises from about 50 ppm to about 100 ppm of peroxyformic acid, e.g., about 50-60 ppm, 60-70 ppm, 70-80 ppm, 80-90 ppm or 90-100 ppm of peroxyformic acid. In yet other embodiments, the first reagent and the second reagent can be configured to be contacted with each other to form a liquid, e.g., a solution, that comprises from about 200 ppm to about 300 ppm of peroxyformic acid, e.g., about 200-210 ppm, 210-220 ppm, 220-230 ppm, 230-240 ppm, 240-250 ppm, 250-260 ppm, 260-270 ppm, 270-280 ppm, 280-290 ppm, 290-300 ppm of peroxyformic acid.

The present peroxyformic acid forming compositions can be configured to form a liquid, e.g., a solution, that comprises any suitable concentration of peroxyformic acid within any suitable time. For example, the first reagent and the second reagent in the present peroxyformic acid forming compositions can be configured to be contacted with each other to form a liquid and/or solid, e.g., a solution, that comprises any suitable concentration of peroxyformic acid within any suitable time. In some embodiments, the first reagent and the second reagent can be configured to be contacted with each other to form a liquid, e.g., a solution, that comprises at least about 1 ppm peroxyformic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, or 5,000 ppm or greater of peroxyformic acid within 1 minute of the contact time.

In an aspect, at least about 1 ppm peroxyformic is generated within less than 1 minute of contacting the first reagent and the second reagent. In an aspect, at least about 1 ppm peroxyformic is generated within less than about 55 seconds, 50 seconds or less, 45 seconds or less, 40 seconds or less, 35 seconds or less, 30 seconds or less, 25 seconds or less, 20 seconds or less, 15 seconds or less, 10 seconds or less, or 5 seconds or less. In an aspect, the reaction to form a liquid comprising at least about 1 ppm peroxyformic acid is near instantaneous. In an aspect, at least about 100 ppm or at least about 500 ppm peroxyformic is generated within about 5 minutes or less of contacting the first reagent and the second reagent. In an aspect, at least about 100 ppm or 500 ppm peroxyformic is generated within less than about 4 minutes, 3 minutes or less, 2 minutes or less, or 1 minute or less.

The present peroxyformic acid forming compositions can be configured to form a liquid, e.g., a solution, that comprises any suitable percentage of the peak concentration of peroxyformic acid within any suitable time. For example, the first reagent and the second reagent in the present peroxyformic acid forming compositions can be configured to be contacted with each other to form a liquid, e.g., a solution, that comprises any suitable percentage of the peak concentration of peroxyformic acid within any suitable time. In some embodiments, the first reagent and the second reagent are configured to be contacted with each other to form a liquid, e.g., a solution, that comprises at least about 80% of the peak concentration of peroxyformic acid within from about 5 minutes to about 15 minutes of the contact time. For example, the first reagent and the second reagent are configured to be contacted with each other to form a liquid, e.g., a solution, that comprises at least about 80%, 85%, 90%, 95%, 96%, 97%, 98%, 99% or 100% of the peak concentration of peroxyformic acid within from about 5 minutes to about 15 minutes of the contact time. In another example, the first reagent and the second reagent are configured to be contacted with each other to form a liquid, e.g., a solution, that comprises at least about 80% of the peak concentration of peroxyformic acid within from about 5, 6, 7, 8, 9, 10, 11, 12, 13, 14 or 15 minutes of the contact time.

The formed peroxyformic acid can maintain any suitable percentage of the peak concentration of peroxyformic acid within any suitable time. In some embodiments, the formed peroxyformic acid can maintain at least about 50% of the peak concentration from about 5 minutes to about 25 minutes after the contact between the first reagent and the second reagent or after the contact between the solid composition and a liquid. For example, the formed peroxyformic acid can maintain at least about 50%, 55%, 60%, 65%, 70%, 75%, 80%, 85%, 90%, 95%, 96%, 97%, 98%, 99% or 100% of the peak concentration from about 5 minutes to about 25 minutes after the contact between the first reagent and the second reagent or after the contact between the solid composition and a liquid. In another example, the formed peroxyformic acid can maintain at least about 50% of the peak concentration from about 5-25 minutes, e.g., about 5, 6, 7, 8, 9, 10, 11, 12, 13, 14, 15, 16, 17, 18, 19, 20, 21, 22, 23, 24 or 25 minutes, after the contact between the first reagent and the second reagent or after the contact between the solid composition and a liquid. In preferred aspects of the methods the desired peak concentration of peroxyformic acid is 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 200 ppm, 300 ppm, 400 ppm, 500 ppm, 600 ppm, 700 ppm, 800 ppm, 900 ppm, 1,000 ppm, 2,000 ppm, 3,000 ppm, 4,000 ppm, 5,000 ppm, 6,000 ppm, 7,000 ppm, 8,000 ppm, 9,000 ppm, 10,000 ppm or more (inclusive of any ranges therein).

The present peroxyformic acid forming compositions can further comprise a C2-C22 percarboxylic acid, and wherein the first reagent or the solid composition comprising the first reagent and the second reagent are kept separately from the C2-C22 percarboxylic acid prior to generate peroxyformic acid. The present peroxyformic acid forming compositions can comprise any suitable $C_2$-$C_{22}$ percarboxylic acid, e.g., peroxyacetic acid, peroxyoctanoic acid and/or peroxysulfonated oleic acid. In an aspect, additional peroxycarboxylic acid compositions can be employed in combination with the peroxyformic acid composition. For example, $C_1$-$C_{24}$ peroxycarboxylic acid, salt of $C_1$-$C_{24}$ peroxycarboxylic acid, ester of $C_1$-$C_{24}$ peroxycarboxylic acid, or mixtures thereof. A carboxylic acid is an organic acid (R—COOH) which contains an aliphatic group and one or more carboxyl groups. A carboxyl group is represented by —COOH, and is usually located at a terminal end of the acid. The aliphatic group can be a substituted or unsubstituted group. Common aliphatic substituents may include —OH, —OR, —NO$_2$, halogen, and other substituents common on these groups. An example of a simple carboxylic acid is acetic acid, which has the formula CH$_3$COOH. A peroxycarboxylic acid is a carboxylic acid which has been oxidized to contain a terminal —COOOH group. The term peroxy acid is often used to represent a peroxycarboxylic acid. An example of a simple peroxy acid is peroxyacetic acid, which has the formula CH$_3$COOOH.

Bleach Component

The bleach component for the methods include a source of active halogen or a halogen releasing substance suitable to liberate active halogen species such-as free elemental halogen (Cl, Br, Cl$_2$, Br$_2$) or —OCl— or —OBr—, under conditions normally used in detergent bleaching cleaning processes of a variety of cleaning targets. Preferably the halogen releasing compound releases chlorine species. Chlorine releasing compounds include potassium dichloroisocyanurate, sodium dichloroisocyanurate, chlorinated trisodium phosphate, sodium hypochlorite, calcium hypochlorite, lithium hypochlorite, monochloramine, dichloramine, [(monotrichloro)-tetra(monopotassium dichloro)] pentaisocyanurate, 1,3-dichloro-5,5-dimethylidantonone, paratoluene sulfodichloro-amide, trichloromelamine, N-chloramine, N-chlorosuccinimide, N,N'-dichloroazodicarbonamide, N-chloroacetyl-urea, N,N-dichlorbiurile, chlorinated dicyandiamide, trichlorocyanuric acid, dichloroglycourea, etc. Chlorinated isocyanurate materials including dichloroisocyanurate dihydrate, sodium dichloroisocyanurate, potassium dichloroisocyanurate, etc. are preferred chlorine sources.

Adjuvants and Additional Functional Ingredients

The components for the methods of antimicrobial sanitizing and/or disinfecting and bleaching laundry can further be combined with various functional components suitable for use in such applications, namely laundry applications. In some embodiments, the steps of dosing a peroxyformic acid composition, an alkalinity source, a bleach activator and/or catalyst in a detergent use solution, and optionally additional hydrogen peroxide make up a large amount, or even substantially all of the total actives dosed into the washing application according to the methods. For example, in some embodiments few or no additional functional ingredients are disposed therein.

In other embodiments, additional functional ingredients may be included in the various dosing steps for the methods. The functional ingredients provide desired properties and functionalities to the peroxyformic acid compositions, the alkalinity agents, and the detergent use solutions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used. For example, many of the functional materials discussed below relate to materials used in a laundry application. However, other embodiments may include functional ingredients for use in other applications.

In other embodiments, the compositions may include defoaming agents, anti-redeposition agents, bleaching agents, solubility modifiers, dispersants, rinse aids, metal protecting agents, stabilizing agents, corrosion inhibitors, additional sequestrants and/or chelating agents, fragrances and/or dyes, rheology modifiers or thickeners, hydrotropes or couplers, buffers, solvents and the like.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Bleaching measurement of a laundry method was performed by a Tergotometer with 1 L pots and a water bath. First, the unwashed swatches from the lot numbers to be used in the test are read on a HunterLab Color Quest Spectrophotometer to establish the average initial (before washing) L value. This L value is a measurement for whiteness on a gray scale. A L value of 0 means black and a L value of 100 means white. A sampling of 25 swatches of each type is used. Next, the wash temperature of 104° F. (40° C.) is programmed into the Tergotometer and its water bath is allowed to heat up to that temperature. One liter of the desired water type is added to each Tergotometer pot and allowed to equilibrate to the temperature.

The bleaching compositions tested were weighed out and added to the Tergotometer pots. The bleaching compositions were agitated for 30 second to 1 minute to mix and dissolve.

Next, the swatches are added quickly to their respective pots in a left to right sequence in order to minimize differences in exposure time to the bleaching systems. During this washing process, agitation is used throughout the process.

At the end of the run, the swatches are removed from the pots quickly in a left to right sequence using a forceps, then squeezed to remove excess water, and finally left out to air dry.

Finally, the swatches are read on the HunterLab Color Quest Spectrophotometer and % soil removal is calculated as follows: % soil removal-(Final L–Initial L)/(96–Initial L)*100.

In this example, PAA and PFA were compared for bleaching efficacy and in some embodiments an alkalinity source (sodium hydroxide) was added and followed by the bleaching component sodium hypochlorite after 5 minutes (examples C and D), then followed by swatches after an additional 1 minute. Tested formulations are shown in Table 1. Corresponding results are depicted in Table 2 and FIG. 1.

TABLE 1

| Formulation | Active | Formulation |
|---|---|---|
| A | NaOCl (50 ppm) | 10% NaOCl<br>89% Water<br>1% NaOH |
| B | PAA (80 ppm) | 31.4% Acetic acid<br>41.3% Water<br>15.2% PAA<br>11.2% H$_2$O$_2$<br>0.9% 1-Hydroxyethane-1,1-disphosphonic acid<br>0.06% Phosphrous acid |
| C | PAA (80 ppm) +<br>NaOCl (50 ppm) | |
| D | PFA (20 ppm) | 6.7% PFA<br>0.74% H$_2$O$_2$<br>74% Formic Acid<br>16.41% Water<br>2.1% methanesulfonic acid<br>0.05% dipicolinic acid |
| E | PFA (20 ppm) +<br>NaOCl (50 ppm) | |

TABLE 2

| Formula | Swatch | L* | a* | b* | Soil Removal [%] |
|---|---|---|---|---|---|
| A | Coffee | 87.05 | 1.18 | 14.19 | 56.18 |
| A | Coffee | 87.03 | 1.19 | 13.93 | 56.08 |
| A | Coffee | 87.01 | 1.19 | 14.23 | 55.98 |
| A | Coffee | 87.07 | 1.16 | 13.94 | 56.28 |
| A | Coffee | 87.38 | 0.9 | 13.84 | 57.79 |
| A | Coffee | 87.31 | 1.01 | 14.32 | 57.45 |
| A | Coffee | 87.42 | 0.99 | 14.04 | 57.99 |
| A | Coffee | 87.34 | 1 | 14.05 | 57.60 |
| A | Tea | 89.24 | 0.29 | 12.28 | 64.56 |
| A | Tea | 89.58 | 0.17 | 11.86 | 66.34 |
| A | Tea | 89.58 | 0.21 | 11.73 | 66.34 |
| A | Tea | 89.47 | 0.19 | 12.04 | 65.76 |
| A | Tea | 89.9 | −0.02 | 12.06 | 68.02 |
| A | Tea | 89.77 | −0.01 | 12.14 | 67.34 |
| A | Tea | 90.12 | −0.1 | 11.6 | 69.17 |
| A | Tea | 89.91 | −0.18 | 12.14 | 68.07 |
| B | Coffee | 77.85 | 2.73 | 12.58 | 11.13 |
| B | Coffee | 77.77 | 2.71 | 12.66 | 10.74 |
| B | Coffee | 77.62 | 2.76 | 12.83 | 10.01 |
| B | Coffee | 77.68 | 2.72 | 12.64 | 10.30 |
| B | Coffee | 77.84 | 2.74 | 12.58 | 11.08 |
| B | Coffee | 77.81 | 2.7 | 12.51 | 10.94 |
| B | Coffee | 78.16 | 2.68 | 12.6 | 12.65 |
| B | Coffee | 78.11 | 2.7 | 12.61 | 12.41 |
| B | Tea | 79.53 | 3.3 | 13.4 | 13.65 |
| B | Tea | 79.68 | 3.29 | 13.54 | 14.43 |
| B | Tea | 79.82 | 3.25 | 13.42 | 15.17 |
| B | Tea | 79.96 | 3.27 | 13.56 | 15.90 |
| B | Tea | 79.92 | 3.22 | 13.53 | 15.69 |
| B | Tea | 79.92 | 3.22 | 13.42 | 15.69 |
| B | Tea | 79.82 | 3.22 | 13.51 | 15.17 |
| B | Tea | 79.83 | 3.25 | 13.42 | 15.22 |
| E | Tea | 87.84 | 1.01 | 13.39 | 57.22 |
| E | Tea | 88.08 | 0.96 | 12.93 | 58.48 |
| E | Tea | 87.94 | 1.01 | 12.85 | 57.74 |
| C | Tea | 80.02 | 3.11 | 13.39 | 16.22 |
| C | Tea | 79.62 | 3.19 | 13.62 | 14.12 |
| C | Tea | 79.51 | 3.16 | 13.58 | 13.54 |
| E | Tea | 88.34 | 0.85 | 12.78 | 59.84 |
| E | Tea | 88.4 | 0.79 | 12.83 | 60.15 |
| E | Tea | 88.77 | 0.63 | 12.76 | 62.09 |
| E | Tea | 88.52 | 0.74 | 12.84 | 60.78 |
| C | Tea | 79.25 | 3.25 | 13.74 | 12.18 |
| C | Tea | 79.66 | 3.11 | 13.59 | 14.33 |
| C | Tea | 79.64 | 3.14 | 13.74 | 14.22 |
| E | Tea | 87.75 | 1.08 | 12.9 | 56.75 |
| E | Tea | 87.8 | 1.08 | 12.88 | 57.01 |
| E | Tea | 87.7 | 1.15 | 13.08 | 56.48 |
| C | Tea | 79.11 | 3.36 | 13.44 | 11.45 |
| C | Tea | 79.26 | 3.31 | 13.32 | 12.23 |
| C | Tea | 79.01 | 3.32 | 13.36 | 10.92 |
| D | Coffee | 77.15 | 2.56 | 12.09 | 7.71 |
| D | Coffee | 76.97 | 2.59 | 12.17 | 6.83 |
| D | Coffee | 77.24 | 2.58 | 12.19 | 8.15 |
| D | Coffee | 77 | 2.59 | 12.2 | 6.97 |
| D | Coffee | 77.16 | 2.52 | 12.18 | 7.76 |
| D | Coffee | 77.46 | 2.47 | 12.05 | 9.22 |
| D | Coffee | 77.06 | 2.41 | 12.08 | 7.27 |
| D | Tea | 79.44 | 3.38 | 13.31 | 13.18 |
| D | Tea | 79.71 | 3.4 | 13.42 | 14.59 |
| D | Tea | 79.46 | 3.42 | 13.43 | 13.28 |
| D | Tea | 79.63 | 3.43 | 13.52 | 14.17 |
| D | Tea | 79.64 | 3.41 | 13.43 | 14.22 |
| D | Tea | 79.77 | 3.41 | 13.51 | 14.91 |
| E | Coffee | 84.83 | 1.98 | 14.42 | 45.31 |
| E | Coffee | 85.22 | 1.91 | 14.53 | 47.22 |
| E | Coffee | 85.11 | 1.99 | 14.6 | 46.68 |
| C | Coffee | 79.09 | 2.53 | 12.56 | 17.21 |
| C | Coffee | 79.13 | 2.51 | 12.6 | 17.40 |
| C | Coffee | 79.04 | 2.5 | 12.59 | 16.96 |
| E | Coffee | 85.45 | 1.88 | 14.53 | 48.35 |
| E | Coffee | 85.47 | 1.88 | 14.47 | 48.44 |
| E | Coffee | 85.38 | 1.94 | 14.86 | 48.00 |
| E | Coffee | 85.46 | 1.88 | 14.63 | 48.39 |
| C | Coffee | 78.17 | 2.57 | 12.75 | 12.70 |
| C | Coffee | 78.1 | 2.57 | 12.67 | 12.36 |
| C | Coffee | 78.05 | 2.6 | 12.68 | 12.11 |
| E | Coffee | 85 | 2.02 | 14.51 | 46.14 |
| E | Coffee | 84.84 | 2.02 | 14.31 | 45.36 |
| E | Coffee | 85.05 | 2.05 | 14.45 | 46.39 |
| C | Coffee | 77.73 | 2.5 | 12.17 | 10.55 |
| C | Coffee | 77.8 | 2.47 | 12.09 | 10.89 |
| C | Coffee | 77.5 | 2.61 | 12.48 | 9.42 |
| C | Coffee | 77.9 | 2.54 | 12.41 | 11.38 |
| C | Coffee | 78.43 | 2.52 | 12.5 | 13.97 |
| C | Coffee | 78.1 | 2.55 | 12.59 | 12.36 |
| C | Tea | 79.55 | 3.1 | 13.53 | 13.75 |
| C | Tea | 79.8 | 3.14 | 13.41 | 15.06 |
| C | Tea | 79.83 | 3.15 | 13.36 | 15.22 |

As shown, the results of this example show the advantage of using a low peroxide component-PFA formula in combination with an additional bleaching component for overall bleaching efficacy. In particular, the results show that PFA does not provide superior bleaching to PAA, but when PAA is combined with a chlorine-bleach component, PAA quenches all of the chlorine and therefore does not exhibit any improvement in bleaching efficacy. However, when PFA is followed with a chlorine-bleach component, the bleaching efficacy of the chlorine bleach is not negatively impacted as there is a demonstrated minimal chlorine quenching due to the low peroxide content of the PFA and to the fact that improved efficacy enables it to be used at lower concentration.

Example 2

For this example, test conditions are shown in Table 3.

TABLE 3

| Time [min] | 10 | 5 |
|---|---|---|
| Experiment 1 Addition | 1.14 g of 3.5% Hydrogen Peroxide | None |
| Experiment 2 Addition | None | 5 g of 1% Bleach |

TABLE 3-continued

| Time [min] | 10 | 5 |
|---|---|---|
| Experiment 3 Addition | 1.14 g of 3.5% Hydrogen Peroxide | 5 g of 1% Bleach |

In Experiments 1 and 3, the Tergotometer was set up for a 10 min cycle. For Experiment 2, the Tergotometer was set up for a 5 min and 30 sec cycle. The pots were each filled with 1 L of 5 grain water. The temperature for all experiments was set to 104° F. Additions to the cycle are shown in Table 3 (times given starting at 10 min and counting down). The wash liquor was immediately titrated after the cycle was complete for available $Cl_2/H_2O_2$. The titrations were completed using 0.01 N Sodium Thiosulfate. Approximately 60 g of wash liquor was poured into a 125 mL Erlenmeyer flask and excess KI and $H_2SO_4$ was added to the solution. The sample was titrated using 0.01N Sodium Thiosulfate, with excess starch added as the end point was approached. After the sample was titrated, a molybdate catalyst was added in excess to react any leftover hydrogen peroxide, and then titrated further as needed.

Results are shown in Table 4 where the available chlorine and hydrogen peroxide titrations (stoichiometric conversions) are shown. The row indicated as "mix" shows that less sodium thiosulfate was consumed, when the two oxidizing substances (NaOCl and $H_2O_2$) were mixed together compared to being left separate. The measured values of $Cl_2$ and $H_2O_2$, are assuming all of the consumed thiosulfate was attributed to either $Cl_2$ or $H_2O_2$.

TABLE 4

| | $Cl_2$ Measured [ppm] | $H_2O_2$ Measured [ppm] | Thiosulfate Consumed/g Sample [µmol/g] |
|---|---|---|---|
| $H_2O_2$ | * | 34.6 | 2.03 |
| NaOCl | 55.1 | * | 1.55 |
| Mix | * | * | 1.35 |

This test indicates where the peracid has an impact on knocking out the bleach in a wash application. This is often referred to as an "Anti-Chlor" effect, referring to whether a chemical or class of chemical neutralize or 'knocks' out chlorine. This is shown by the mixing of the NaOCl and $H_2O_2$ where there is no additive or additional effect, confirming that the $H_2O_2$ has the effect of knocking out the chlorine bleach. This demonstrates according to the methods the benefit of employing a low peroxide peroxyformic acid composition.

Example 3

Microefficacy performance comparison between PAA and PFA formulations on *Klebsiella pneumoniae* (ATCC 4352) was compared at a dosing temperature of 40° C. for 5 minutes of contact. Three sterile swatches (1"×1.5") were inoculated with 0.03 mL of a prepared suspension containing *Klebsiella pneumoniae*. The carriers were then dried until visibly dry and aseptically placed between the sixth and seventh folds of a fabric wound spindle. The spindle was then placed into a chamber. Solutions of PFA and PAA were then added to the chamber (75 g). The chamber was secured into a laundrometer and run for 5 minutes at 40° C. After 5 minutes, the carriers were neutralized separately and then diluted and plated to calculate log reductions. The wash water was also neutralized and then diluted and plated to calculate log reductions.

PAA was dosed at a labeled rate for disinfection of textiles at (4 oz/cwt; 60 gal/cwt for a 15.2% active solution). Table 5 shows the performance of PAA at concentrations from 20 ppm to 80 ppm in comparison to a PFA formulation with less than 20 ppm (17 ppm).

TABLE 5

| Test Substance Concentration | Coupon Log Reduction *Klebsiella* |
|---|---|
| PAA 80 ppm | >4.02 |
| PAA 60 ppm | >3.90 |
| PAA 40 ppm | 3.15 |
| PAA 20 ppm | 2.07 |
| PFA 17 ppm | >5.12 |

As shown in Table 5 the PFA composition provided superior sanitizing and/or disinfecting properties at a significantly lower actives when compared to PAA. This data is significant as a lower ppm/active level of a antimicrobial sanitizing and/or disinfecting peroxyformic acid composition can be dosed into wash (such as laundry), including at low temperatures to provide bacterial kill without consuming or neutralizing the bleach compositions due to the lower active level and lower hydroxide content of the peroxyformic acid composition.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A method of antimicrobial treatment sanitizing and/or disinfecting and bleaching laundry, the method comprising:
    (a). washing the laundry with between about 5 ppm to about 200 ppm of a peroxyformic acid composition at a pH range from about 4 to about 7 in a laundry washing machine for effective antimicrobial efficacy on the laundry, wherein there is optionally a draining of the peroxyformic acid composition before adding the alkalinity step; thereafter
    (b). adding an alkalinity source to the washing machine to increase the pH range to at least about 7 in the laundry washing machine, wherein there is optionally a draining step before adding the chlorine bleach; thereafter
    (c). applying a chlorine bleach component in the laundry washing machine; and
    (d). draining the peroxyformic acid composition and the chlorine bleach component from the laundry.

2. The method of claim 1, wherein the laundry washing machine is an industrial machine or a consumer machine.

3. The method of claim 1, wherein the peroxyformic acid composition is applied to the laundry in the laundry washing machine at a pH from about 5 to about 7.

4. The method of claim 1, wherein the peroxyformic acid composition is applied to the laundry in the laundry washing machine for about 3 to about 15 minutes.

5. The method of claim 1, wherein the peroxyformic acid composition comprises peroxyformic acid, formic acid and hydrogen peroxide.

6. The method of claim 1, wherein the peroxyformic acid composition is provided to the laundry washing machine at an actives level from about 5 ppm to about 80 ppm.

7. The method of claim 1, wherein the alkalinity source increases the pH range to at least above 10.

8. The method of claim 1, wherein the chlorine bleach component is applied to the laundry in the laundry washing machine for about 3 to about 15 minutes.

9. The method of claim 8, wherein the chlorine bleach component is hypochlorite.

10. The method of claim 1, wherein the chlorine bleach component is a chlorine releasing component comprising one or more of dichloroisocyanurate, chlorinated trisodium phosphate, hypochlorite, monochloramine, dichloramine, [(monotrichloro)-tetra(monopotassium dichloro)] pentaisocyanurate, 1,3-dichloro-5,5-dimethylidantonone, paratoluene sulfodichloro-amide, trichloromelamine, N-chloramine, N-chlorosuccinimide, N,N'-dichloroazodicarbonamide, N-chloroacetyl-urea, N,N-dichlorbiurile, chlorinated dicyandiamide, trichlorocyanuric acid, and dichloroglycourea.

11. The method of claim 1, wherein the peroxyformic acid composition further comprises any one or more of surfactants, chelants, polymers, enzymes, defoaming agents, anti-redeposition agents, stabilizing agents, solubility modifiers, dispersants, rinse aids, metal protecting agents, stabilizing agents, corrosion inhibitors, sequestrants, fragrances, dyes, rheology modifiers or thickeners, hydrotropes or couplers, buffers, and solvents.

12. The method of claim 11, wherein the laundry is optionally rinsed with water in the laundry washing machine following the chlorine bleach step for at least about 1 minute.

13. The method of claim 1, wherein the method further comprises applying an adjuvant use solution comprising at least one of souring agents, fabric softening agents, starch, anti-wrinkle agents, sizing agents, color-fastness agents, oil and water repellant agents, water conditioning agents, iron controlling agents, water threshold agents, soil releasing agents, soil shielding agents, optical brightening agents, fragrances, and mixtures thereof at any point in the method of antimicrobial treatment sanitizing and/or disinfecting and bleaching laundry.

14. The method of claim 13, wherein the adjuvant use solution is applied to the laundry in the laundry washing machine at a pH from about 5 to about 8 for about 1 to about 6 minutes.

15. The method of claim 1, wherein the method of antimicrobial sanitizing and/or disinfecting and bleaching laundry disinfects and/or sanitizes the laundry and removes bacteria, viruses or other contaminants from the laundry.

16. The method of claim 15, wherein the antimicrobial step kills the bacteria, viruses or other contaminants before any wash waters are discharged from the laundry washing machine.

17. The method of claim 1, wherein the temperature of the washing machine is less than about 120° F.

18. The method of claim 1, wherein the method of antimicrobial sanitizing and/or disinfecting and bleaching laundry follows an initial washing step for the laundry.

* * * * *

UNITED STATES PATENT AND TRADEMARK OFFICE
CERTIFICATE OF CORRECTION

PATENT NO. : 10,513,673 B2
APPLICATION NO. : 16/015391
DATED : December 24, 2019
INVENTOR(S) : Jason Lang et al.

Page 1 of 1

It is certified that error appears in the above-identified patent and that said Letters Patent is hereby corrected as shown below:

In the Claims

<u>In Column 31, Claim 10, Line 20:</u>
DELETE "dimethylidantonone" before "paratoluene"
INSERT --dimethylhydantoin-- before "paratoluene"

Signed and Sealed this
Third Day of March, 2020

Andrei Iancu
*Director of the United States Patent and Trademark Office*